(12) United States Patent
Chermak

(10) Patent No.: US 6,422,975 B1
(45) Date of Patent: Jul. 23, 2002

(54) WRIST/HAND MOBILITY ENHANCER/EXERCISER

(76) Inventor: Eugene F. Chermak, 323 Bordic Rd., Reading, PA (US) 19606-3606

( * ) Notice: Subject to any disclaimer, the term of this patent is extended or adjusted under 35 U.S.C. 154(b) by 0 days.

(21) Appl. No.: 09/924,145

(22) Filed: Aug. 8, 2001

(51) Int. Cl.[7] ............................................. A63B 23/14
(52) U.S. Cl. .......................... 482/46; 482/44; 482/45; 482/127
(58) Field of Search ............................ 482/44–48, 127; 601/5, 33, 40; 602/21, 22

(56) References Cited

U.S. PATENT DOCUMENTS

| | | | | |
|---|---|---|---|---|
| 2,233,764 A | * | 3/1941 | Bauermeister | 482/127 |
| 2,832,334 A | * | 4/1958 | Whitelaw | 128/25 |
| 5,113,849 A | * | 5/1992 | Kuiken et al. | 128/26 |
| 5,135,217 A | * | 8/1992 | Swain | 273/4.5 |
| 5,271,617 A | * | 12/1993 | Gilford | 273/1.5 A |
| 5,413,554 A | * | 5/1995 | Trueman | 602/21 |
| 5,437,620 A | * | 8/1995 | Shelly | 602/21 |
| 5,476,439 A | * | 12/1995 | Robinson | 601/40 |
| 5,820,577 A | * | 10/1998 | Taylor | 601/40 |
| 5,876,363 A | * | 3/1999 | Marx | 602/21 |
| 5,976,058 A | * | 11/1999 | Gustafson | 482/44 |
| 6,080,090 A | * | 6/2000 | Taylor | 482/121 |
| 6,241,643 B1 | * | 6/2001 | Loft et al. | 482/114 |

* cited by examiner

Primary Examiner—Michael A. Brown
Assistant Examiner—Lori Baker Amerson
(74) Attorney, Agent, or Firm—Donald R. Schoonover

(57) ABSTRACT

An exercise device for enhancing the mobility of a user who may be suffering from tendinitis of the wrist. The device includes a forearm brace portion that is hingeably connected to a hand brace portion with a spring element connecting the two brace portions together. The spring element can be changed to vary the resistance against which the user works. Straps and loops connect portions of the user's hand and forearm to the device.

9 Claims, 2 Drawing Sheets

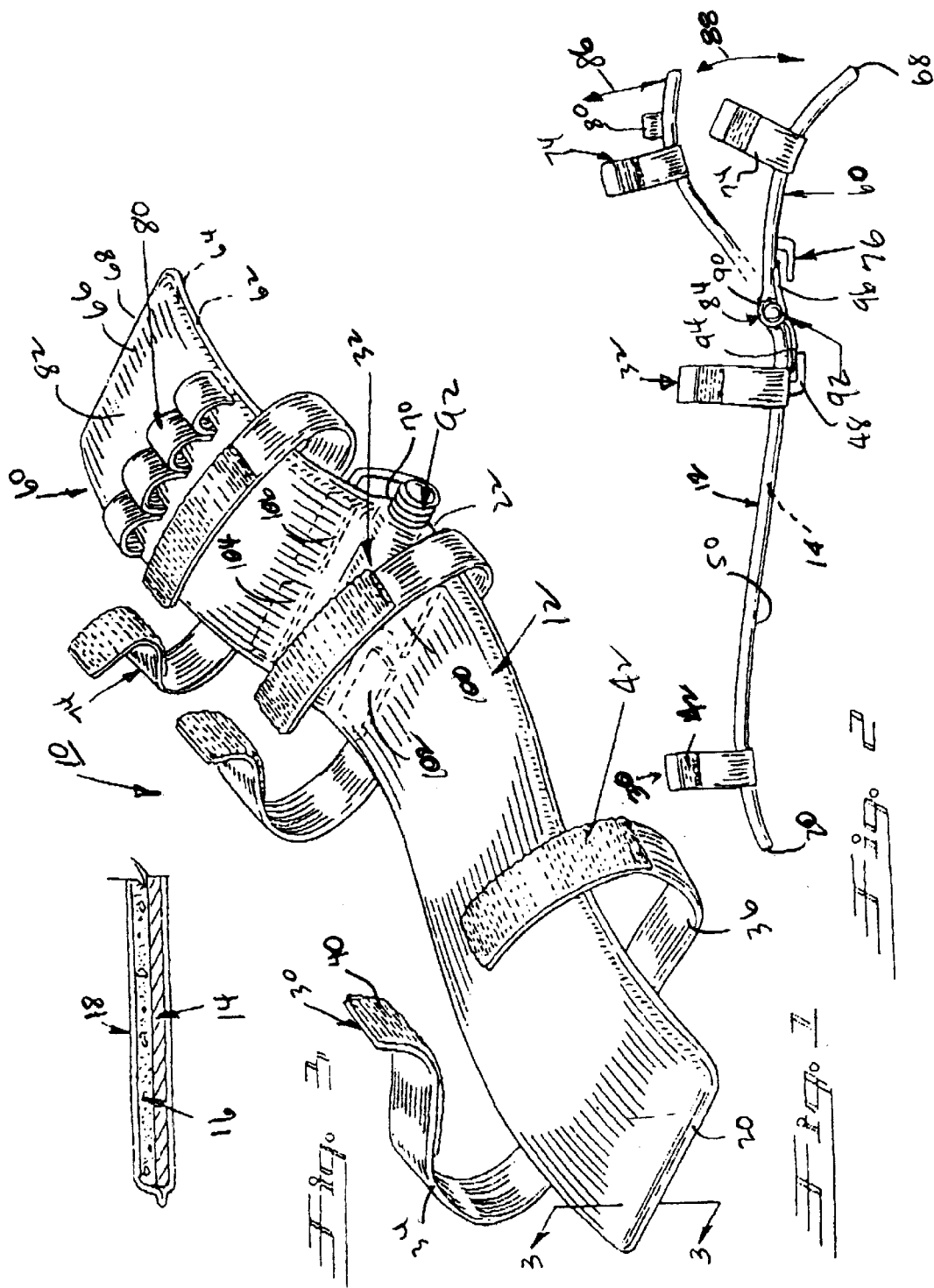

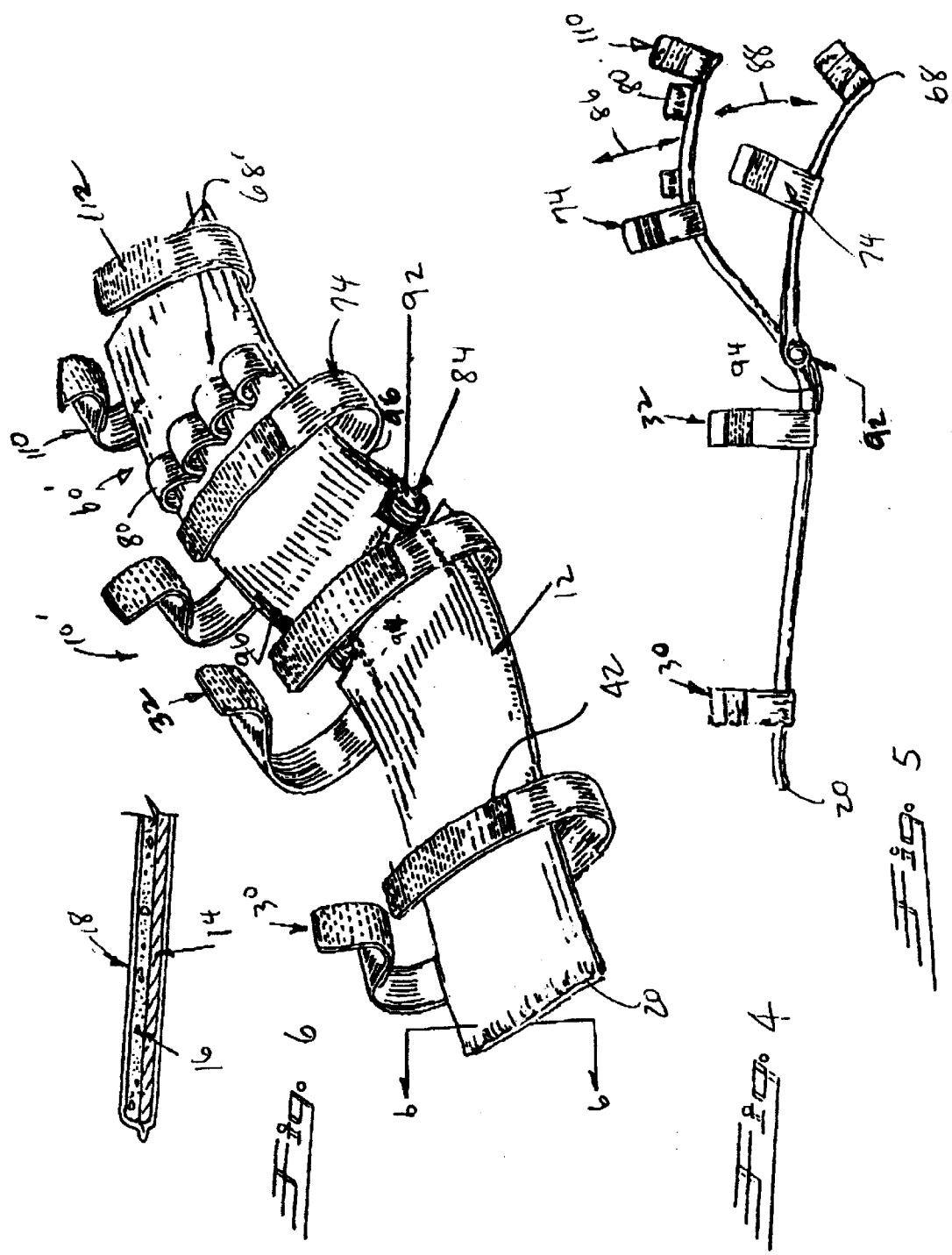

WRIST/HAND MOBILITY ENHANCER/EXERCISER

BACKGROUND OF THE INVENTION

1. Field of the Invention

The present invention relates to the general art of exercise and kinestherapy devices, and to the particular field of hand and/or wrist devices.

2. Discussion of the Related Art

Today, more and more people are engaging in a wider and wider variety of physical activities. As more people engage in such activities, the incidence of injuries increases. Such injuries range from "weekend warrior" bumps and bruises and sprains to extremely serious injuries.

Furthermore, many occupations create situations where a worker is in danger of suffering an injury. Such injuries include repetitive stress injuries as well as sprains, bruises and the like.

Accordingly, many rehabilitation centers and devices have proliferated. However, many of the rehabilitation devices are expensive and complicated. In fact, some such devices cannot be used by all potential patients because the devices are either too expensive or too difficult to use.

Therefore, there is a need for a rehabilitation device that is inexpensive and easy to use, even for elderly and infirm patients.

Tendinitis is a very common ailment. In particular, tendinitis of the wrist is fairly common. However, in spite of the many rehabilitation devices available, the inventor is not aware of any such device which is as inexpensive and as easy to use as possible. Thus, improvement of such rehabilitation devices is possible and desirable.

Accordingly, there is a need for an improved rehabilitation device which is useful in treating tendinitis, especially tendinitis of the wrist.

Still further, some rehabilitation devices are not as comfortable as possible. For example, the devices may be heavy, or may require a user to twist his or her appendage in an uncomfortable way, or the like. For this reason, some rehabilitation devices are not used as often or as vigorously as possible, and full advantage is not taken of such devices.

Therefore, there is a need for a rehabilitation device which is comfortable.

Still further, many rehabilitation devices must be cleaned after a certain number of uses. However, due to the construction of many existing rehabilitation devices, cleaning is difficult or complicated. For this reason, some rehabilitation devices are not cleaned as often as they should be.

Therefore, there is a need for a rehabilitation device that can be easily and efficiently cleaned.

Still further, some rehabilitation devices must be securely held in place in order to be fully effective. In fact, if such a device is not properly held in place, its effectiveness may be totally vitiated, and may even be harmful. However, it is not always possible to hold a rehabilitation device securely in place because the user is injured or simply not strong enough to hold the device as securely as required to obtain safe and effective use of the device. The device should be securely held in place in a manner that is comfortable and effective if the device is to be properly used.

Therefore, there is a need for a rehabilitation device that is securely held in place on a user during use without requiring undue effort by the user.

There is a further need for a rehabilitation device that is securely, yet comfortably, held in place on a user during use without requiring undue effort by the user.

A further requirement of an effective rehabilitation device is that it be versatile. That is, the device should be amenable to use by a wide range of users for a wide range of abilities and disabilities if the device is to be most effectively used. Thus, the device should be easy to alter to match the needs of the user. The resistance to movement of such devices is used to strengthen a user and such resistance should be variable in order to meet all of the needs of the users. It is even more desirable if the user can effect the adjustment without the aid of a consultant.

Therefore, there is a need for a rehabilitation device that can be easily adjusted to meet the particular needs of the user.

PRINCIPAL OBJECTS OF THE INVENTION

It is a main object of the present invention to provide a rehabilitation device that is inexpensive and easy to use, even for elderly and infirm patients.

It is another object of the present invention to provide a rehabilitation device which is useful in treating tendinitis, especially tendinitis of the wrist.

It is another object of the present invention to provide a rehabilitation device which is comfortable.

It is another object of the present invention to provide a rehabilitation device that can be easily and efficiently cleaned.

It is another object of the present invention to provide a rehabilitation device that is securely held in place on a user during use without requiring undue effort by the user.

It is another object of the present invention to provide a rehabilitation device that is securely, yet comfortably, held in place on a user during use without requiring undue effort by the user.

It is another object of the present invention to provide a rehabilitation device that can be easily adjusted to meet the particular needs of the user.

SUMMARY OF THE INVENTION

These, and other, objects are achieved by a wrist/hand exerciser which includes a forearm brace portion hingeably connected to a hand brace portion with a spring removably mounted thereon. The device of the present invention includes a steel frame on which a pad is placed with a cover removably enclosing these two elements. Straps and loops are strategically located on the device to comfortably, yet securely, attach the device to a user in a proper position. The device is shaped for comfortably fitting on the user.

In this manner, the user can comfortably, effectively and efficiently perform his or her rehabilitation exercises. After completion of a training session, the cover is easily removed for cleaning.

The device of the present invention is particularly suited to rehabilitating someone with tendinitis, especially tendinitis of the wrist.

BRIEF DESCRIPTION OF THE DRAWINGS

FIG. 1 is a perspective view of a preferred form of the wrist/hand exerciser embodying the teaching of the present invention.

FIG. 2 is a side elevational view of the device shown in FIG. 1.

FIG. 3 is a section view taken along line 3—3 of FIG. 1.

FIG. 4 is a perspective view of another form of the wrist/hand exerciser embodying the teaching of the present invention.

FIG. 5 is a side elevational view of the device shown in FIG. 4.

FIG. 6 is a section view taken along line 6—6 of FIG. 3.

DETAILED DESCRIPTION OF THE INVENTION

Other objects, features and advantages of the invention will become apparent from a consideration of the following detailed description and the accompanying drawings.

The rehabilitation device of the present invention is most useful in rehabilitating a person who has tendinitis in his or her wrist. The device is easily adjusted and is easily cleaned, yet is comfortable and versatile.

As shown in FIGS. 1–3, a wrist/hand mobility exerciser 10 embodying the present invention comprises: a forearm portion 12 which abuts a user's forearm from the user's wrist towards the user's elbow when exerciser 10 is in place on the user. Forearm portion 12 includes a first monolithic, one-piece steel frame 14 which, as is best seen in FIG. 2, is in the shape of an ogee curve to be comfortably worn by the user on his or her forearm. The plate can be high tensile plastic if suitable. The forearm portion further includes a first monolithic, one-piece pad 16 on the first steel frame 14 so the exerciser does not place a steel plate against a user's skin. A first monolithic, one-piece cover 18 is removably mounted on pad 16 and on first steel frame 14 of forearm portion 12 so that the cover can easily be removed, cleaned and replaced after each use of exerciser 10.

Forearm portion 12 further includes a distal end 20 and a proximal end 22, with proximal end 22 being located adjacent to a user's wrist when exerciser 10 is in place on the user.

Forearm brace portion 12 is removably attached to a user by means of a first forearm attaching strap 30 on forearm brace portion 12 near distal end 20 of forearm brace portion 12 and a second forearm attaching strap 32 on forearm brace portion 12 near proximal end 22 of forearm brace portion 12. Both of the straps 30 and 32 include two strap portions, such as strap portions 34 and 36 of strap 30, with each strap portion including a fastener, such as strips of hook-and-loop fastener material 40 and 42, thereon. The straps can be closed over the user's forearm and pulled as tight as desired and then connected together using the fasteners on the straps. This permits the user to easily and quickly adjust the fit of exercise device 10 to his or her own comfort range while the device is held in place for proper use.

A first spring seat 48 is located on surface 50 on forearm brace portion 12 near proximal end 22 of forearm brace portion 12 for a purpose that will be understood from this disclosure.

Exerciser 10 further includes a hand brace portion 60 which is curved to comfortably and securely fit against a user's palm when exerciser 10 is being used. Hand brace portion 60 is concave in shape with respect to the user's palm as can be seen in FIG. 2.

Hand brace portion 60 includes a second monolithic, one-piece steel frame 62, a second monolithic, one-piece pad 64 on second steel frame 62 and a second monolithic, and a one-piece cover 66 removably mounted on pad 64 and on second steel frame 62 of hand brace portion 60.

Hand brace portion 60 further includes a distal end 68, and a proximal end 70, with proximal end 70 located adjacent to proximal end 22 of forearm brace portion 12 and being located to be adjacent to a user's wrist when exerciser 10 is on the user. Hand brace portion 60 is attached to a user's hand by means of elements such as a first hand attaching strap 74 on hand brace portion 60 near proximal end 70 of hand brace portion 60 to be located near a user's interdigital pads when in use, with attaching strap 74 being similar to straps 30 and 32 to attach a user's hand to exerciser 10 in a secure yet comfortable manner.

A second spring seat 76 is located on hand brace portion 60 near proximal end 70 of hand brace portion 60. A plurality of finger loops, such as loop 80, are located on surface 82 of hand brace portion 70 near hand attaching strap 74 on hand brace portion 60 for securely holding a user's fingers in place and in proper position and orientation for proper use of exerciser 10.

A hinge portion 84 connects hand brace portion 60 to forearm brace portion 12 together in a manner that permits the portions to move with respect to each other as indicated by arrows designated by numerals 86 and 88 in FIG. 2, with two positions of hand brace portion 60 being shown.

A spring sleeve 90 is located on hinge portion 84 and a spring element 92 is removably mounted in spring sleeve 90 and has one end 94 removably received in first spring seat 48 on forearm brace portion 12 and a second end 96 removably received in second spring seat 76 on hand brace portion 60.

It is noted that the cover for both the forearm brace portion and the hand brace portion can be combined into a fabric cover with a foam cushion in place of the two separate elements discussed above. It is also noted that different size elements can be used if the exerciser is to be used with a child or with an adult. In one case, the forearm brace portion can be twelve inches inoverall length and three to four inches in width with a 3/16" thick plastic plate. One form of the spring is a piano spring, with springs being used that offer upward force as well as downward force and variable forces as will occur to those familiar with the spring art. Color coding can also be used to help a user identify the spring of his or her choice.

As will be understood by those skilled in the art, exerciser 10 is attached to a user by attaching straps 30 and 32 together over the user's forearm, inserting the user's fingers into loops 80 and attaching strap 74 together over the user's hand. The user then moves his or her hand relative to his or her forearm to move hand brace portion 60 in the direction indicated in FIG. 2 by arrows 86 and 88 which are double-headed to indicate the back and forth movement of the user's hand during use of exerciser 10. Different spring elements 92 can be inserted and/or removed from spring sleeve 84 to adjust and change the tension against which the user works according to the exercise routine for that user.

As can be seen in FIG. 1, spring ends 94 and 96 abut against spring end abutment pads 100, 102, 104, 106 on the forearm brace portion and on the hand brace portion near the proximal ends 22 and 70 respectively. These pads protect the spring and the brace portions from wear and tear from the spring ends as the exerciser is moved in directions indicated by arrows 86 and 88.

An alternative form of the exerciser is shown in FIGS. 4–6 as exerciser 10'. Exerciser 10' is similar to exerciser 10, except that exerciser 10' includes a second hand attaching strap 110 on hand brace portion 60' near distal end 68' of hand brace portion 60' and omits the spring seats and spring end abutment pads. Strap 110 is identical to hand strap 74 and includes a fastener, such as hook-and-loop fastener 112, thereon to fix strap 110 to a user's hand near the fingers of the user. This provides a more secure attachment of exerciser 10' to the user, if such more secure attachment is desired.

Otherwise, exerciser 10' is identical to exerciser 10 and thus will not be further discussed.

It is understood that while certain forms of the present invention have been illustrated and described herein, it is not to be limited to the specific forms or arrangements of parts described and shown.

I claim:

1. A wrist/hand mobility exerciser comprising:
   a) a forearm brace portion which includes
      (1) a first monolithic, one-piece steel frame,
      (2) a first monolithic, one-piece pad on said first steel frame,
      (3) a first monolithic, one-piece cover removably mounted on said pad and on said first steel frame of said forearm brace portion,
      (4) a distal end,
      (5) a proximal end,
      (6) a first forearm attaching strap on said forearm brace portion near said distal end of said forearm brace portion,
      (7) a second forearm attaching strap on said forearm brace portion near said proximal end of said forearm brace portion, and
      (8) a first spring seat on said forearm brace portion near said proximal end of said forearm brace portion;
   b) a hand brace portion which includes
      (1) a second monolithic, one-piece steel frame,
      (2) a second monolithic, one-piece pad on said second steel frame,
      (3) a second monolithic, one-piece cover removably mounted on said second pad and on said second steel frame of said hand brace portion,
      (4) a distal end,
      (5) a proximal end,
      (6) a first hand attaching strap on said hand brace portion near said proximal end of said hand brace portion,
      (7) a second spring seat on said hand brace portion near said proximal end of said hand brace portion, and
      (8) a plurality of finger loops on said hand brace portion near said first hand attaching strap on said hand brace portion;
   c) a hinge portion connecting said hand and forearm brace portions together;
   d) a spring sleeve on said hinge portion; and
   e) a spring element removably mounted in said spring sleeve and having one end removably received in said first spring seat on said forearm brace portion and a second end removably received in said second spring seat on said hand brace portion.

2. The wrist/hand mobility exerciser as described in claim 1 wherein each strap includes a hook-and-loop fastener section.

3. The wrist/hand mobility exerciser as described in claim 2 further including a first spring end abutment pad mounted on said forearm brace portion adjacent to said first spring seat on said forearm brace portion, and a second spring end abutment pad mounted on said hand brace portion adjacent to said second spring seat on said hand brace portion.

4. The wrist/hand mobility exerciser as described in claim 3 wherein said second forearm attaching strap on said forearm brace portion is positioned immediately adjacent to said first spring seat on said forearm brace portion.

5. The wrist/hand mobility exerciser as described in claim 4 further including a third spring end abutment pad mounted on said forearm brace portion adjacent to said first spring seat on said forearm brace portion and a fourth spring end abutment pad mounted on said hand brace portion adjacent to said second spring seat on said hand brace portion.

6. The wrist/hand mobility exerciser as described in claim 5 wherein said forearm brace portion is in the form of an ogee curve.

7. The wrist/hand mobility exerciser as described in claim 6 wherein said hand brace portion is in the form of a concave curve with respect to the wearer's palm when said hand brace portion is in place on a user.

8. The wrist/hand mobility exerciser as described in claim 7 further including a second hand attaching strap on said hand brace portion near said distal end of said hand brace portion.

9. A wrist/hand mobility enhancer comprising:
   a) a forearm brace portion which includes
      (1) a first monolithic, one-piece frame element,
      (2) a cover pad on said first frame element,
      (3) a distal end,
      (4) a proximal end,
      (5) a first forearm attaching strap on said forearm brace portion near said distal end of said forearm brace portion, and
      (6) a second forearm attaching strap on said forearm brace portion near said proximal end of said forearm brace portion;
   b) a hand brace portion which includes
      (1) a second monolithic, one-piece frame element,
      (2) a cover pad on said second frame element,
      (3) a distal end,
      (4) a proximal end,
      (5) a first hand attaching strap on said hand brace portion near said proximal end of said hand brace portion, and
      (6) a plurality of finger loops on said hand brace portion near said first hand attaching strap on said hand brace portion;
   c) a hinge portion connecting said hand and forearm brace portions together;
   d) a spring sleeve on said hinge portion; and
   e) a spring element removably mounted in said spring sleeve and having one end abutting said forearm brace portion and a second end abutting said hand brace portion.

* * * * *